United States Patent [19]

Hamprecht et al.

[11] Patent Number: 5,104,441
[45] Date of Patent: Apr. 14, 1992

[54] HERBICIDAL SULFONAMIDES AND THEIR USE TO INFLUENCE PLANT GROWTH

[75] Inventors: Gerhard Hamprecht, Weinheim; Helmut Hagen, Frankenthal, both of Fed. Rep. of Germany; Thomas Liese-Sauer, Sao Bernardo do Campo, Brazil; Norbert Meyer, Ladenburg; Bruno Wuerzer, Otterstadt, both of Fed. Rep. of Germany

[73] Assignee: BASF Aktiengesellschaft, Ludwigshafen, Fed. Rep. of Germany

[21] Appl. No.: 618,587

[22] Filed: Nov. 28, 1990

Related U.S. Application Data

[63] Continuation of Ser. No. 464,652, Jan. 11, 1990, abandoned, which is a continuation of Ser. No. 195,138, May 17, 1988, abandoned.

[30] Foreign Application Priority Data

May 19, 1987 [DE]  Fed. Rep. of Germany ....... 3716657

[51] Int. Cl.$^5$ ................... A01N 43/54; C07D 239/69; C07D 239/42
[52] U.S. Cl. ........................................ 71/92; 544/321; 544/332
[58] Field of Search ...................... 71/92; 544/321, 332

[56] References Cited

U.S. PATENT DOCUMENTS

| | | | |
|---|---|---|---|
| 4,383,113 | 5/1983 | Levitt | 71/92 |
| 4,547,215 | 10/1985 | Wolf | 71/92 |
| 4,566,898 | 1/1986 | Reap | 71/93 |
| 4,592,978 | 6/1986 | Levitt | 71/92 |
| 4,661,147 | 4/1987 | Dumas | 71/92 |

FOREIGN PATENT DOCUMENTS 0174212  3/1986  European Pat. Off. .

Primary Examiner—John M. Ford
Attorney, Agent, or Firm—Keil & Weinkauf

[57] ABSTRACT

Substituted sulfonylureas of the formula I

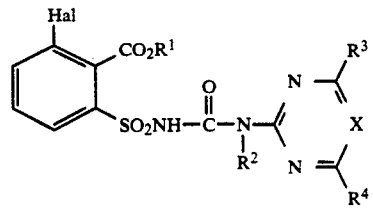

where
$R^1$ is hydrogen, $C_1$–$C_4$-alkyl, $C_3$–$C_4$-alkenyl or alkynyl, $C_1$–$C_4$-haloalkyl, $C_3$–$C_6$-alkoxyalkyl, $C_4$–$C_6$-haloalkoxyalkyl or $C_5$–$C_6$-cycloalkyl,
$R^2$ is hydrogen, methyl or ethyl,
$R^3$ is hydrogen, halogen, methyl or methoxy,
$R^4$ is hydrogen, methyl or methoxy,
X is N or C—H,
and Hal is fluorine, chlorine or bromine, and alkali metal or alkaline earth metal salts thereof, with the proviso that $R^1$ is not methyl when Hal is chlorine and X is N, a process for the manufacture of sulfonylureas of the formula I and their use as herbicides.

9 Claims, No Drawings

HERBICIDAL SULFONAMIDES AND THEIR USE TO INFLUENCE PLANT GROWTH

This application is a continuation of Ser. No. 07/464,652, filed Jan. 11, 1990, which is a continuation of Ser. No. 195,138, filed May 17, 1988, both now abandoned.

The present invention relates to novel substituted 6-halo-2-[[(1,3,5-triazin-2-yl or 1,3-pyrimindin-2-yl)aminocarbonyl]aminosulfonyl]benzoic acid esters, processes for their preparation, herbicides and plant growth regulators which contain the novel compounds as active ingredients, and a process for controlling and suppressing plant growth by means of these compounds.

European Patent EP 7687 describes sulfonylurea derivatives having a herbicidal action.

It is an object of the present invention to provide novel compounds having improved properties.

We have found, surprisingly, that this object is achieved with substituted sulfonyl ureas of the formula

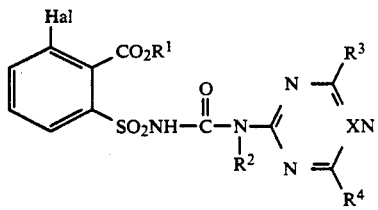

where
R$^1$ is hydrogen, C$_1$–C$_4$-alkyl, C$_3$–C$_4$-alkenyl, or C$_3$–C$_4$-alkynyl, C$_1$–C$_4$-haloalkyl, C$_3$–C$_6$-alkoxyalkyl, C$_4$–C$_6$-haloalkoxyalkyl or C$_5$–C$_6$-cycloalkyl,
R$^2$ is hydrogen, methyl or ethyl,
R$^3$ is hydrogen, halogen, methyl or methoxy,
R$^4$ is hydrogen, methyl or methoxy,
X is N or C—H and Hal is fluorine, chlorine or bromine, or their alkali metal salts or alkaline earth metal salts, which compounds and salts are well tolerated by certain crops, for example Indian corn.

The end products of the formula I not only constitute a technical advance but also meet a major economic requirement, namely that they selectively control species of millet. Thus, M. Hanf in BASF Mitteilungen für den Landbau, 1/85, Ackerunkräuter und Ackergräser - ihre Verbreitung, Gefährdung und wirtschaftliche Bedeutung states, on page 23: "Dioctyledonous weeds can easily by controlled with triazines, The spaces cleared were however also taken over by species of millet which, like the Indian corn itself, are resistant to this group of agents (triazines). These millets are above all species of the genera Echinochloa, Digitaria and etaria. It is now necessary to repress these species, in turn, by other specific control agents and methods."

This requirement, discussed in the light of practical experience, can now be met by the compounds according to the application.

Preferred end products of the formula I are those in which R$^1$ is hydrogen, C$_1$–C$_4$-alkyl, i.e. methyl, ethyl, preferably n-propyl, isopropyl, n-butyl, isobutyl, sec-butyl or tert.-butyl, C$_3$–C$_4$-alkenyl or C$_3$–C$_4$-alkynyl, such as allyl, methallyl, crotyl, but-1-en-3-yl, propargyl, but-1-yn-3-yl, or but-2-ynyl, C$_1$–C$_4$-haloalkyl, such as 2-chloroethyl, 2-chloro-n-propyl, 3-chloro-n-propyl, 1-chloro-but-2-yl, 2-chloroisobutyl, 4-chloro-n-butyl, chloro-tert.-butyl, 3-chloro-prop-2-yl and 2,2,2-trifluoroethyl, C$_3$–C$_6$-alkoxyalkyl, such as 2-methoxyethyl, 2-ethoxyethyl, 3-methoxy-n-propyl, 2-methoxy-n-propyl, 3-methoxy-n-butyl, 1-methoxy-but-2-yl, methoxy-tert.butyl, ethoxy-tert.-butyl, 2methoxy-n-butyl, 4methoxy-n-butyl, 2-ethoxy-n-propyl, 3-methoxy-n-prop-2-yl, 2-ethoxy-n-but-1-yl or 4-ethoxy-n-butyl, C$_4$–C$_6$-haloalkoxyalkyl, such as 2-($\beta$-chloroethoxy)ethyl, 3($\beta$-chloroethoxy)-n-propyl or 3-($\gamma$-chloro-n-propoxy)n-propyl, or C$_5$–C$_6$-cycloalkyl, such as cyclopentyl or cyclohexyl.

The sulfonyl ureas of the formula I are obtained, for example, by (a) reacting a compound of the formula

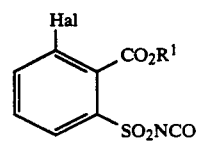

where R$^1$ has the above meaning and Hal is halogen, with a compound of the formula III

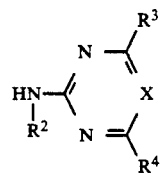

where R$^2$, R$^3$, R$^4$ and X have the above meanings, in the presence or absence of an inert organic solvent, at a temperature conventionally used for organic reactions, namely from 0° C. to 120° C., preferably from 10° C. to 100° C. The reaction may be carried out at atmospheric or superatmospheric pressure, continuously or batchwise.

If methyl 6-fluoro-2-isocyanatosulfonylbenzoate and 2-amino-4-methoxy-6-methyl-1,3,5-triazine are used as starting materials, the course of the reaction can be represented by the following equation:

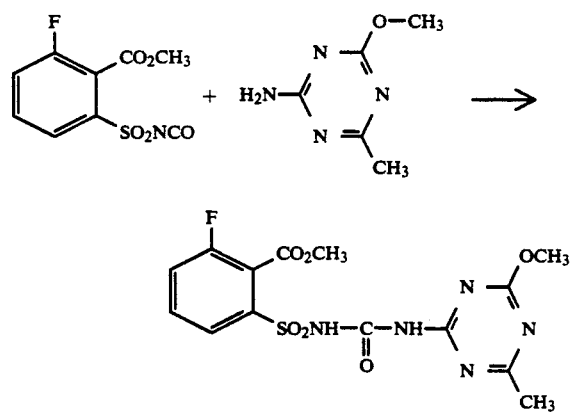

The sulfonyl ureas of the formula I may also be obtained (b) by reacting a sulfonamide of the formula

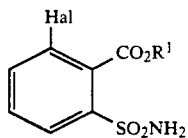   IV where $R^1$ has the above meaning and Hal is halogen, with a phenyl carbamate of the formula

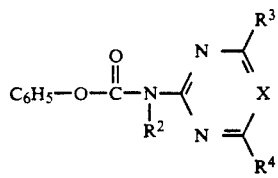   V where $R^2$, $R^3$, $R^4$ and X have the above meanings, in the presence or absence of an inert organic solvent and in the presence or absence of a tertiary base, at a temperature conventionally used for organic reactions, namely from 0° C. to 120° C., preferably from 10° C. to 100° C.

If, for example, methyl 6-fluoro-2-aminosulfonylbenzoate and phenyl-N-(4-methoxy-1,3,5-triazin-2-yl)carbamate are used as starting materials, the course of the reaction can be represented by the following equation:

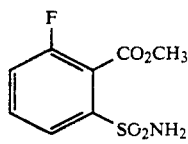

+

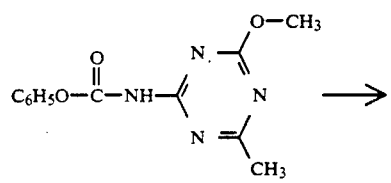

→

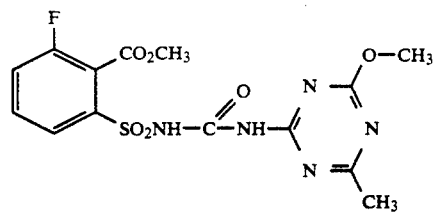

The sulfonyl ureas of the formula I may also be obtained (c) by reacting a phenyl carbamate of the formula

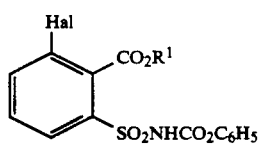   VI where $R^1$ has the above meaning and Hal is halogen, with an amine of the formula

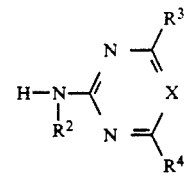   III where $R^2$, $R^3$, $R^4$ and X have the above meanings, in the presence or absence of an inert organic solvent and in the presence or absence of a tertiary base, at a temperature conventionally used for organic reactions, namely from 0° C. to 120° C., preferably from 10° C. to 100° C.

If, for example, methyl 6-fluoro-2-(phenoxycarbamolsulfonyl)benzoate and 2-amino-4-methoxy-6-methyl-1,3,5-triazine are used as starting materials, the course of the reaction can be represented by the following equation:

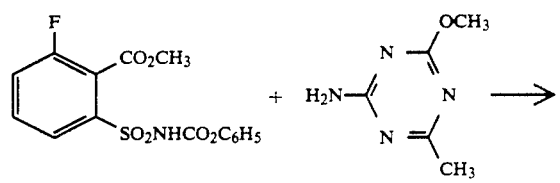

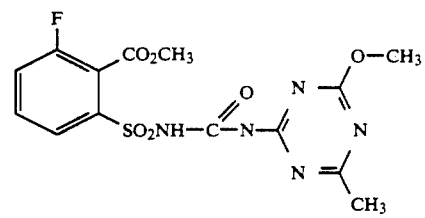

Advantageously, the reaction is carried out in a solvent or diluent which is inert under the particular reaction conditions. Examples of suitable solvents are halo hydrocarbons, especially chlorohydrocarbons, e.g. tetrachloroethylene, 1,1,2,2-tetrachloroethylene, 1,1,1,2-tetrachloroethane, dichloropropane, methylene chloride, dichlorobutane, chloroform, chloronaphthalene, dichloronaphthalene, carbon tetrachloride, 1,1,1-trichloroethane or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o- or p- or m-dibromobenzene, o-, m- or p-chlorotoluene or 1,2,4-trichlorobenzen; ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or $\beta$, $\beta'$-dichlorodiethyl ether; nitrohydrocabons, such as nitromethane, nitroethane, nitrobenzene o-, m- or p-chloronitrobenzene or o-nitrotoluene; nitroles, such as acetonitirle, butyronitrile; isobutyronitrile, benzonitrile and m-chlorobenzonitrile; aliphatic or cycloaliphatic hydrocarbons, e.g. heptane, pinane, nonane, o-, m- and p-cymol, gasoline fractions boiling within a range from 70° C. to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, e.g. ethyl acetate, ethyl acetoacetate or isobutyl acetate; amides, e.g. formamide, methylformamide or dimethylformamide; ketones, e.g. acetone, methyl ethyl ketone and mixtures of the above. The solvent is advantageously used in an amount of from 100% to 2,000% by weight, preferably from 200% to 700% by weight, based on starting materials II, IV or VI.

The compounds III or V required for the reaction are in general employed in about equimolar amounts (with an excess or deficiency of, for example, 0% to 20%, based on the particular starting materials II, IV or VI). The starting materials II, IV or VI may be introduced into one of the above diluents, after which the starting material III, in the cause of reaction (a) and (c), or the starting material V in the case of reaction (b), is added.

Advantageously, however, the process for the preparation of the novel compound is carried out by taking the starting material III or V, with or without one of the above diluents, and then adding starting material II (in the reaction a) or IV (in reaction b) or VI (in reaction c).

To complete the reaction, the mixture is stirred, after combining the components, for from 20 minutes to 24 hours at from 0° C. to 120° C., preferably from 10° C. to 100° C., especially from 20° C. to 80° C.

A tertiary base, e.g. pyridine, $\alpha,\beta\gamma$-picoline, 2,4-lutidine, 2,6-lutidine, 2,4,6-collidine, p-dimethylaminopyridine, 1,4-diaza[2,2,2]bicyclooctane [DABCO] or 1,8-diazabicyclop[5,4,0]-undec-7-en, in an amount of from 0.01 to 1 mol per mol of starting material IV or VI, may advantageously be used as a reaction accelerator in reaction (b) or (c).

The salts of the sulfonyl ureas obtained by reaction with a stoichiometric amount of an aqueous base or of a metal alcoholate, if appropriate in an inert organic solvent.

The end product I is isolated from the mixture resulting from reactions a-c in the conventional manner, for example by distilling off the solvent or directly by filtering off under suction. The residue obtained may be washed with water or dilute acid to remove basic impurities. However, the residue may also be dissolved in a water-immiscible solvent, the solution then being washed as described. The desired end products are thereby obtained in a pure form but can, where necessary, be purified by recrystallization or chromatography.

Compounds of the formula I, where $R^1$ is hydrogen, are obtained by hydrolysis of esters of the formula I, where $R^1$ is $C_1$-$C_4$-alkyl. The hydrolysis is carried out with not less than a two fold amount of a base such as sodium hydroxide or potassium hydroxide, advantageously in a solvent mixture comprising from 2 to 8 parts by weight of methanol and from 10 to 40 parts by weight of water per part by weight of the ester of the formula II, at from 30° C. to 80° C. for from 1 to 20 hours. The sulfonamidocarboxylic acids of the formula I are precipitated by acidification.

The sulfonamides required as starting materials of the formula IV may be prepared by a Meerwein reaction from 6-halo-anthranilic acid esters and subsequent reaction with ammonia.

EXAMPLE OF THE PREPARATION OF THE INTERMEDIATE METHYL 6-CHLORO-2-AMINOSULFONYL-BENZOATE 93 g of 4-chloro-1,2-benzisothiazol-3-one-1,1-dioxide were suspended in 0.8 l of methanol and stirred for 3 hours under reflux, while passing hydrogen chloride gas through the mixture. After cooling to 20° C., suction filtration and drying, 60 g of the compound shown in the title, of melting point 152° C.-153° C., were obtained. Concentration of the filtrate under reduced pressure, trituration of the residue with methyl tert.-butyl ether, filtering off under suction and drying gave 42 g of a second fraction of melting point from 144° C.-149° C.

The following compounds of the general structure shown below can either be obtained similarly or have been prepared, in those cases where physical data are shown.

| R | m.p. (°C.) | m.p. (°C.) |
|---|---|---|
| $C_2H_5$ | 97-101 | 129-131 |
| n-$C_3H_7$ | 111-113 | 104-107 |
| i-$C_3H_7$ | 145-147 | 84-87 |
| n-$C_4H_9$ | | |
| i-$C_4H_9$ | | |
| sek. $C_4H_9$ | | |
| $CH_2$—CH=$CH_2$ | 105-108 | |
| $CH_2$—C≡CH | | |
| $CH_2$—$CH_2$—Cl | 130-134 | 109-110 |
| $CH_2$—$CH_2$—O—$CH_3$ | 102-104 | 135-136 |
| $CH_2$—$CH_2$—O—$CH_2CH_2$—Cl | 124-126 | |
| Cyclohexyl | | |

EXAMPLE OF THE PREPARATION OF THE INTERMEDIATE METHYL 6-CHLORO-2-ISOCYANATOSULFONYL-BENZOATE 100 g of methyl 6-chloro-2-aminosulfonyl-benzoate were suspended in 300 ml of 1,2-dichloroethane, 123 g of thionuyl chloride were added with stirring, and the mixture was slowly heated to the reflux temperature. After it had been stirred for 5 hours under reflux, it was cooled to 55° C., 1.5 ml of pyridine were added and the mixture again heated to the reflux temperature, while introducing phosgene. After 4 hours' treatment with phosgene gas, the reaction mixture was concentrated under reduced pressure and flushed with nitrogen. The oil which remained (105 g) was used, without further purification, for the subsequent stages.

EXAMPLE OF THE PREPARATION OF THE INTERMEDIATE METHYL 6-FLUORO-2-CHLOROSULFONYL-BENZOATE 108 g of methyl 6-fluoroanthranilate and 45 g of sodium nitrite in 106 ml of water were added, via 2 feed devices, to 250 ml of stirred concentrated hydrochloric acid at 5° C. over the course of 1 hour in such a way that the ester component was present in excess. After the reaction mixture had been stirred for 20 minutes at 55° C.-8° C. it was poured, in one shot, into a previously prepared solution of 53 g of sulfur dioxide, 1.7 g of copper(II) chloride and a small amount of water in 200 ml of 1,2-dichloroethane, and the resulting mixture was stirred for 10 minutes thereafter. It was then slowly heated to 50° C. and stirred for 1½ hours while introducing 46 g of sulfur dioxide. It was then cooled to 20° C. and 5.5 g of chlorine were introduced over 20 minutes, with stirring. Stirring was then continued for 20 minutes, after which the organic phase was separated off. It was washed with water, dried over magnesium sulfate and evaporated, giving 105 g of the compound shown in the title, in the form of a brownish oil.

EXAMPLE OF THE PREPARATION OF THE INTERMEDIATE METHYL 6-FLUORO-2-AMINOSULFONYL-BENZOATE 42.5 g of ammonia gas were introduced, at 20° C.-28° C., into a stirred mixture of 252.5 g of methyl 6-fluoro-2-chlorosulfonyl-benzoate in 700 ml of anhydrous tetrahydrofuran. After the batch had been stirred for one hour at 25° C. the precipitate formed was filtered off with suction and dissolved in water, and the solution was extracted once with ethyl acetate. On acidifying the aqueous phase with concentrated hydrochloric acid, 8.8 g of 4-fluoro-1,2-benzisothiazol-3-one-1,1-dioxide of melting point 210° C.-212° C. were obtained as a by-product.

The tetrahydrofuran filtrate was concentrated, precipitated with water, the precipice taken up in ethyl acetate, again precipitated with water, filtered off with suction and dried. 186 g of the compound shown in the title, of melting point 155° C.-159° C., were obtained. 4-Fluoro-1,2-benzisothiazol-3-one-1,1-dioxide.

100 g of methyl 6-fluoro-2-aminosulfonyl-benzoate were introduced into 430 ml of 1N sodium hydroxide solution and the mixture was heated to 40° C. and stirred for a further 5 minutes. It was then acidified with concentrated hydrochloric acid and the batch stirred for 20 minutes. After filtering off the product with suction, washing it with water and drying it, 74.4 g of the compound shown in the title, of melting point 210° C.-212° C., were obtained.

EXAMPLE 1

Methyl 6-chloro-2-[[(4,6-dimethyl-1,3-pyrimindin-2-yl)aminocarbonyl]aminosulfonyl]benzoate 15 g of methyl 6-chloro-2-(isocyanatosulfonyl)-benzoate in 100 ml of absolute acetonitirle were added over 10 minutes, at room temperature, to a stirred suspension of 6.7 g of 2-amino-4,6-dimethylpyrmidine in 50 ml of absolute acetonitirle under nitrogen; the temperature rose by 6° C. After having stirred for 5 hours at 25° C., the precipitate formed was filtered off with suction, washed with 1N dihydrochloric acid and with methanol and dried. 14.2 g of the compound shown in the title, of melting point 215° C.-217° C. were obtained.

EXAMPLE 2

β-Methoxyethyl 6-fluoro-2-[[(4,6-dimethoxy-1,3,5-triazin-2-yl)aminocarbonyl]aminosulfonyl]benzoate 7.1 g of β-methoxyethyl 6-fluoro-2-isocyanatosulfonylbenzoate in 20 ml of methylene chloride were added over 10 minutes at 25° C. to a stirred mixture of 4 g of 2-amino-4,6-dimethoxy-1,3,5-triazine in 40 ml of DMF under nitrogen; the temperature rose to 32° C. After the mixture had been stirred for 14 hours at 25° C., the solvent was removed under reduced pressure and the residue was stirred with ether and twice with 3N HCL. It was then taken up in acetone, insoluble mater was separated off and the filtrate was concentrated to dryness. 7 g of the compound shown in the title, of melting point 179° C.-182° C. were obtained.

EXAMPLE 3

Sodium salt of isopropyl 6-chloro-2-[[(4,6-dimethoxy-1,3,5-triazin-2-yl)aminocarbonyl]aminosulfonyl]benzoate 4.6 g of isopropyl 6-chloro-2-[[4,6-dimethoxy-1,3,5-triazin-2-yl) aminocarbonyl]aminosulfonyl]benzoate (compound 133) were suspended in 100 ml of methanol, 1.8 g of 30% strength methanolic sodium methylate was added at 25° C. and the mixture was heated 5 minutes to 50° C. until a clear solution was obtained. After concentrating under reduced pressure, 4.7 g of the compound shown in the title, of melting point 185° C. (with decomposition) were obtained.

The following compounds were prepared in accordance with the foregoing example (in which case physical characteristics are given) or may be prepared analogously.

TABLE 1

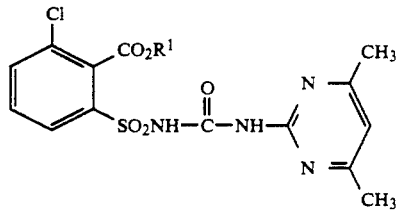

| Example | $R^1$ | mp (°C.) |
|---|---|---|
| 4 | $C_2H_5$ | 198–200 |
| 5 | n-$C_3H_7$ | |
| 6 | i-$C_3H_7$ | 200–202 |
| 7 | n-$C_4H_9$ | |
| 8 | i-$C_4H_9$ | |
| 9 | sec-$C_4H_9$ | |
| 10 | $CH_2-CH=CH_2$ | |
| 11 | $CH_2-C\equiv CH$ | |
| 12 | $CH_2-CH_2Cl$ | |
| 13 | $CH_2-CH_2-O-CH_3$ | |
| 14 | $CH_2-CH_2-O-CH_2-CH_2Cl$ | |
| 15 | cyclohexyl | |

TABLE 2

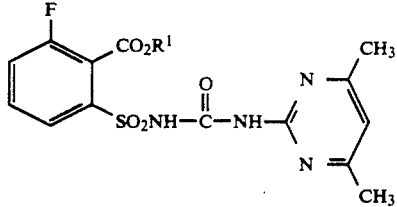

| Example | $R^1$ | mp (°C.) |
|---|---|---|
| 16 | $CH_3$ | 212–214 |
| 17 | $C_2H_5$ | |
| 18 | i-$C_3H_7$ | |
| 19 | n-$C_4H_9$ | |
| 20 | i-$C_4H_9$ | |
| 21 | sec-$C_4H_9$ | |
| 22 | $CH_2-CH=CH_2$ | |
| 23 | $CH_2-C\equiv CH$ | |
| 24 | $CH_2-CH_2Cl$ | |
| 25 | $CH_2-CH_2-O-CH_3$ | 158–160 |
| 26 | $CH_2-CH_2-O-CH_2-CH_2Cl$ | |
| 27 | cyclohexyl | |

TABLE 3

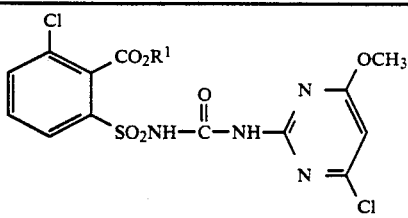

| Example | R[1] | mp (°C.) |
|---|---|---|
| 28 | CH$_3$ | 213 decomp. |
| 29 | C$_2$H$_5$ | 179–182 |
| 30 | n-C$_3$H$_7$ | 181–184 |
| 31 | i-C$_3$H$_7$ | 210–212 |
| 32 | n-C$_4$H$_9$ | |
| 33 | i-C$_4$H$_9$ | |
| 34 | sec-C$_4$H$_9$ | |
| 35 | CH$_2$—CH=CH$_2$ | |
| 36 | CH$_2$—C≡CH | |
| 37 | CH$_2$—CH$_2$Cl | 169–171 |
| 38 | CH$_2$—CH$_2$—O—CH$_3$ | 168–170 |
| 39 | CH$_2$—CH$_2$—O—CH$_2$—CH$_2$Cl | 161–164 |
| 40 | cyclohexyl | |

TABLE 4

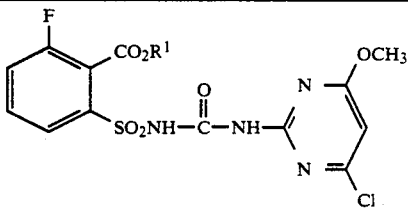

| Example | R[1] | mp (°C.) |
|---|---|---|
| 41 | CH$_3$ | 215–217 |
| 42 | C$_2$H$_5$ | 210–213 |
| 43 | n-C$_3$H$_7$ | 195–198 |
| 44 | i-C$_3$H$_7$ | |
| 45 | n-C$_4$H$_9$ | |
| 46 | i-C$_4$H$_9$ | |
| 47 | sec-C$_4$H$_9$ | |
| 48 | CH$_2$—C=CH$_2$ | |
| 49 | CH$_2$—C≡CH | |
| 50 | CH$_2$—CH$_2$Cl | |
| 51 | CH$_2$—CH$_2$—O—CH$_3$ | 175–177 |
| 52 | CH$_2$—CH$_2$—O—CH$_2$—CH$_2$Cl | |
| 53 | cyclohexyl | |

TABLE 5

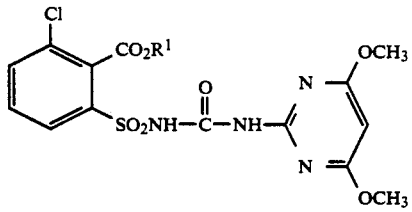

| Example | R[1] | mp (°C.) |
|---|---|---|
| 54 | CH$_3$ | 227–230 |
| 55 | C$_2$H$_5$ | 210–212 |
| 56 | n-C$_3$H$_7$ | 217–219 |
| 57 | i-C$_3$H$_7$ | 202–205 |
| 58 | n-C$_4$H$_9$ | |
| 59 | i-C$_4$H$_9$ | |
| 60 | sec-C$_4$H$_9$ | |
| 61 | CH$_2$—CH=CH$_2$ | 197 decomp. |
| 62 | CH$_2$—C≡CH | |
| 63 | CH$_2$—CH$_2$Cl | |
| 64 | CH$_2$—CH$_2$—O—CH$_3$ | 173–175 |

TABLE 5-continued

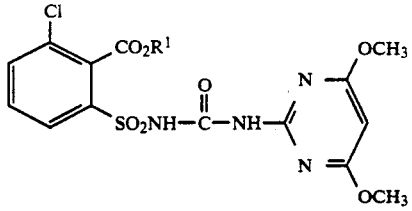

| Example | R[1] | mp (°C.) |
|---|---|---|
| 65 | CH$_2$—CH$_2$—O—CH$_2$—CH$_2$Cl | |
| 66 | cyclohexyl | |

TABLE 6

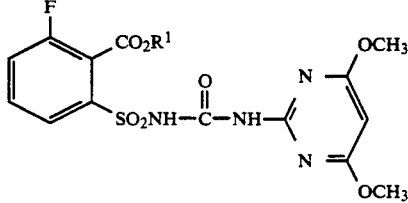

| Example | R[1] | mp (°C.) |
|---|---|---|
| 67 | CH$_3$ | 204–206 |
| 68 | C$_2$H$_5$ | |
| 69 | n-C$_3$H$_7$ | |
| 70 | i-C$_3$H$_7$ | |
| 71 | n-C$_4$H$_9$ | |
| 72 | i-C$_4$H$_9$ | |
| 73 | sec-C$_4$H$_9$ | |
| 74 | CH$_2$—CH=CH$_2$ | |
| 75 | CH$_2$—C≡CH | |
| 76 | CH$_2$—CH$_2$Cl | |
| 77 | CH$_2$—CH$_2$—O—CH$_3$ | |
| 78 | CH$_2$—CH$_2$—O—CH$_2$—CH$_2$Cl | |
| 79 | cyclohexyl | |

TABLE 7

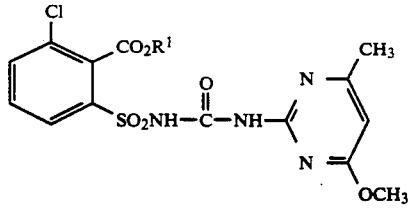

| Example | R[1] | mp (°C.) |
|---|---|---|
| 80 | CH$_3$ | 210–214 |
| 81 | C$_2$H$_5$ | 193–195 |
| 82 | n-C$_3$H$_7$ | 178–180 |
| 83 | i-C$_3$H$_7$ | 205–207 |
| 84 | n-C$_4$H$_9$ | |
| 85 | i-C$_4$H$_9$ | |
| 86 | sec-C$_4$H$_9$ | |
| 87 | CH$_2$—CH=CH$_2$ | |
| 88 | CH$_2$—C≡CH | |
| 89 | CH$_2$—CH$_2$Cl | 153 decomp. |
| 90 | CH$_2$—CH$_2$—O—CH$_3$ | 154–156 |
| 91 | CH$_2$—CH$_2$—O—CH$_2$—CH$_2$Cl | 149–151 |
| 92 | cyclohexyl | |

TABLE 8

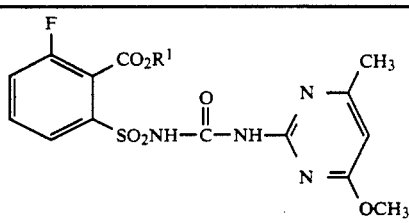

| Example | R¹ | mp (°C.) |
|---|---|---|
| 93 | $CH_3$ | 190-192 |
| 94 | $C_2H_5$ | |
| 95 | $n-C_3H_7$ | |
| 96 | $i-C_3H_7$ | |
| 97 | $n-C_4H_9$ | |
| 98 | $i-C_4H_9$ | |
| 99 | $sec-C_4H_9$ | |
| 100 | $CH_2-CH=CH_2$ | |
| 101 | $CH_2-C\equiv CH$ | |
| 102 | $CH_2-CH_2Cl$ | 170-171 |
| 103 | $CH_2-CH_2-O-CH_3$ | 160-162 |
| 104 | $CH_2-CH_2-O-CH_2-CH_2Cl$ | |
| 105 | cyclohexyl | |

TABLE 9

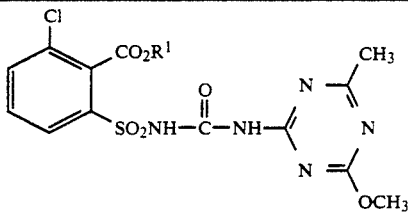

| Example | R¹ | mp (°C.) |
|---|---|---|
| 106 | $C_2H_5$ | 192-194 |
| 107 | $n-C_3H_7$ | 179-181 |
| 108 | $i-C_3H_7$ | 197-198 |
| 109 | $n-C_4H_9$ | |
| 110 | $i-C_4H_9$ | |
| 111 | $sec-C_4H_9$ | |
| 112 | $CH_2-CH=CH_2$ | |
| 113 | $CH_2-C\equiv CH$ | |
| 114 | $CH_2-CH_2Cl$ | |
| 115 | $CH_2-CH_2-O-CH_3$ | |
| 116 | $CH_2-CH_2-O-CH_2-CH_2Cl$ | |
| 117 | cyclohexyl | |

TABLE 10

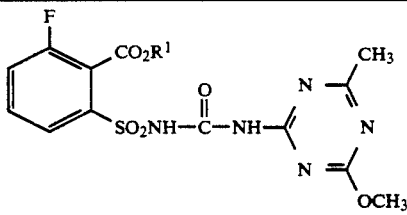

| Example | R¹ | mp (°C.) |
|---|---|---|
| 118 | $CH_3$ | 212-213 |
| 119 | $C_2H_5$ | 196 decomp. |
| 120 | $n-C_3H_7$ | 196-199 |
| 121 | $i-C_3H_7$ | 199-201 |
| 122 | $n-C_4H_9$ | |
| 123 | $i-C_4H_9$ | |
| 124 | $sec-C_4H_9$ | |
| 125 | $CH_2-CH=CH_2$ | |
| 126 | $CH_2-C\equiv CH$ | |
| 127 | $CH_2-CH_2Cl$ | |
| 128 | $CH_2-CH_2-O-CH_3$ | 153-156 |
| 129 | $CH_2-CH_2-O-CH_2-CH_2Cl$ | |

TABLE 10-continued

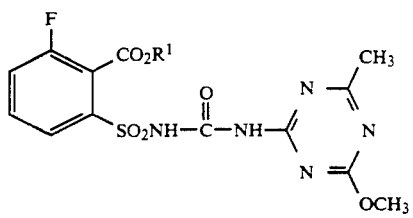

| Example | R¹ | mp (°C.) |
|---|---|---|
| 130 | cyclohexyl | |

TABLE 11

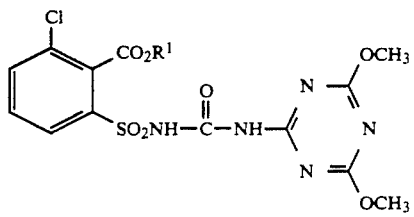

| Example | R¹ | mp (°C.) |
|---|---|---|
| 131 | $C_2H_5$ | 202 decomp. |
| 132 | $n-C_3H_7$ | |
| 133 | $i-C_3H_7$ | 218-220 |
| 134 | $n-C_4H_9$ | |
| 135 | $i-C_4H_9$ | |
| 136 | $sec-C_4H_9$ | |
| 137 | $CH_2-CH=CH_2$ | |
| 138 | $CH_2-C\equiv CH$ | |
| 139 | $CH_2-CH_2Cl$ | 194-196 |
| 140 | $CH_2-CH_2-O-CH_3$ | |
| 141 | $CH_2-CH_2-O-CH_2-CH_2Cl$ | 198 decomp. |
| 142 | cyclohexyl | |

TABLE 12

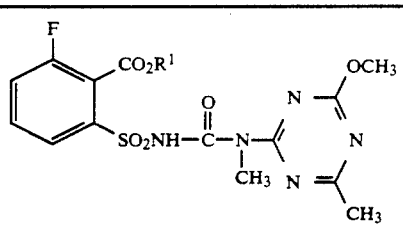

| Example | R¹ | mp (°C.) |
|---|---|---|
| 143 | $CH_3$ | |
| 144 | $C_2H_5$ | |
| 145 | $n-C_3H_7$ | |
| 146 | $i-C_3H_7$ | |
| 147 | $n-C_4H_9$ | |
| 148 | $i-C_4H_9$ | |
| 149 | $sec-C_4H_9$ | |
| 150 | $CH_2-CH=CH_2$ | |
| 151 | $CH_2-C\equiv CH$ | |
| 152 | $CH_2-CH_2Cl$ | |
| 153 | $CH_2-CH_2-O-CH_3$ | |
| 154 | $CH_2-CH_2-O-CH_2-CH_2Cl$ | |
| 155 | cyclohexyl | |

TABLE 13

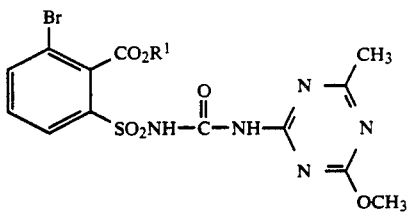

| Example | R¹ | mp (°C.) |
|---|---|---|
| 156 | $CH_3$ | 202–205 |
| 157 | $C_2H_5$ | |
| 158 | $n-C_3H_7$ | |
| 159 | $i-C_3H_7$ | 197–199 |
| 160 | $n-C_4H_9$ | |
| 161 | $i-C_4H_9$ | |
| 162 | $sec-C_4H_9$ | |
| 163 | $CH_2-CH=CH_2$ | |
| 164 | $CH_2-C\equiv CH$ | |
| 165 | $CH_2-CH_2Cl$ | |
| 166 | $CH_2-CH_2-O-CH_3$ | |
| 167 | $CH_2-CH_2-O-CH_2-CH_2Cl$ | |
| 168 | cyclohexyl | |

TABLE 14

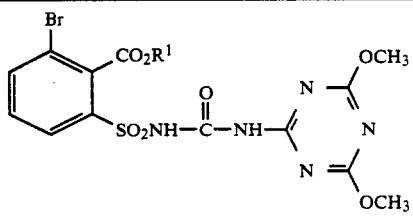

| Example | R¹ | mp (°C.) |
|---|---|---|
| 169 | $CH_3$ | 216–218 |
| 170 | $C_2H_5$ | |
| 171 | $n-C_3H_7$ | |
| 172 | $i-C_3H_7$ | 210 decomp. |
| 173 | $n-C_4H_9$ | |
| 174 | $i-C_4H_9$ | |
| 175 | $sec-C_4H_9$ | |
| 176 | $CH_2-CH=CH_2$ | |
| 177 | $CH_2-C\equiv CH$ | |
| 178 | $CH_2-CH_2Cl$ | |
| 179 | $CH_2-CH_2-O-CH_3$ | |
| 180 | $CH_2-CH_2-O-CH_2-CH_2Cl$ | |
| 181 | cyclohexyl | |

TABLE 15

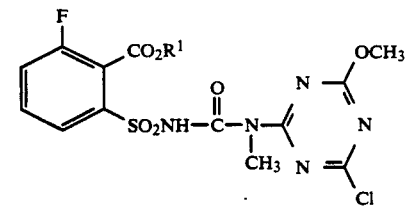

| Example | R¹ | mp (°C.) |
|---|---|---|
| 182 | $CH_3$ | |
| 183 | $C_2H_5$ | |
| 184 | $n-C_3H_7$ | |
| 185 | $i-C_3H_7$ | |

TABLE 16

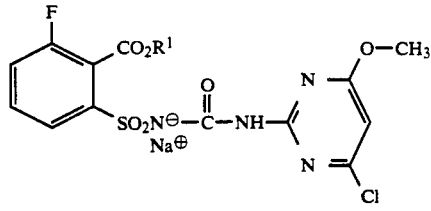

| Example | R¹ | mp (°C.) |
|---|---|---|
| 186 | $CH_3$ | >300 |
| 187 | $C_2H_5$ | >300 |
| 188 | $n-C_3H_7$ | >300 |
| 189 | $i-C_3H_7$ | |
| 190 | $n-C_4H_9$ | |
| 191 | $i-C_4H_9$ | |
| 192 | $sec.-C_4H_9$ | |
| 193 | $CH_2-CH=CH_2$ | |
| 194 | $CH_2-CH_2Cl$ | |
| 195 | $CH_2-CH_2-O-CH_3$ | 167 decomp. |

TABLE 17

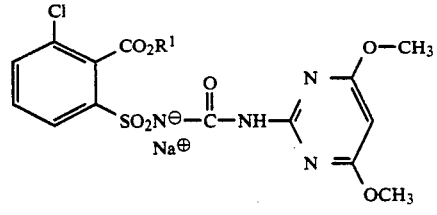

| Example | R¹ | mp (°C.) |
|---|---|---|
| 196 | $CH_3$ | |
| 197 | $C_2H_5$ | |
| 198 | $n-C_3H_7$ | |
| 199 | $CH_2-CH_2-O-CH_3$ | 154 |

TABLE 18

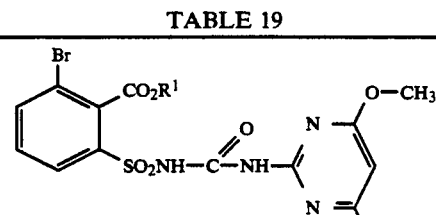

| Example | R¹ | mp (°C.) |
|---|---|---|
| 200 | $CH_3$ | |
| 201 | $C_2H_5$ | >300 |
| 202 | $n-C_3H_7$ | |

TABLE 19

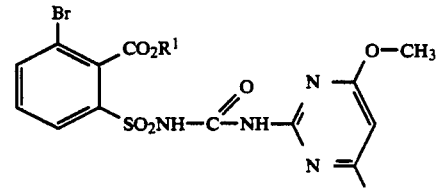

| Example | R¹ | mp (°C.) |
|---|---|---|
| 203 | $CH_3$ | 225–228 |
| 204 | $C_2H_5$ | |

TABLE 19-continued

Structure: 2-bromo-6-(CO₂R¹)-phenyl-SO₂NH—C(=O)—NH—[4-methoxy-6-chloropyrimidin-2-yl]

| Example | R¹ | mp (°C.) |
|---|---|---|
| 205 | n-C₃H₇ | |

The active ingredients, or herbicidal agents containing them, may be applied pre- or postemergence. If certain crop plants tolerate the active ingredients less well, application techniques may be used in which the herbicidal agents are sprayed from suitable equipment in such a manner that the leaves of the sensitive crop plants are if possible not touched, and the agents reach the soil or the unwanted plants growing beneath the crop plants (post-directed, lay-by treatment).

The amounts applied depend on the time of year, the plants to be combated and their growth stage, and vary from 0.001 to 1, and preferably from 0.005 to 0.5, kg/ha.

The herbicidal action of sulfonamides of the formula I on the growth of these plants is illustrated in greenhouse experiments described below.

The vessels employed were plastic flowerpots having a volume of 300 cm³, and which were filled with a sandy loam containing about 3.0% humus. The seeds of the tests plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rates were 0.015, 0.03, 0.04 and 0.06 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment varied and were for example 0.015, 0.03, 0.06 and 0.125 kg of active ingredient per hectare. No covers were placed on the vessels in this method.

The pots were set up in the greenhouse—species from warmer areas at from 20° C. to 35° C., and species from moderate climates at 10° C. to 20° C. The experiments were run for 2to 4 weeks. During this period the plants were tended and their reactions to the various treatments assessed. The scale employed was 0 to 100, 100 denoting nonemergence or complete destruction of at least the visible plant parts, and 0 denoting no damage or normal emergence.

The influence of the treatments was assessed visually against the untreated control.

The plants used in the greenhouse experiments were weeds and crop plants for example of the following species:

| Abbreviation | Latin name | Common name |
|---|---|---|
| AMARE | Amaranthus retroflexus | redroot pigweed |
| CHEAL | Chenopodium album | lambsquarters (goosefoot) |
| CHYCO | Chrysanthemum coronarium | crown daisy |
| CYPES | Cyperus esculatus | yellow nutsedge |
| CYPIR | Cyperus iria | rice flatsedge |
| ECHCG | Echinochloa cruss-galli | barnyardgrass |
| IPOSS | Ipomoea spp. | morningglory |
| LAMAM | Lamium amplexicaule | henbit |
| LOLMU | Lolium multi-florum | Italian ryegrass |
| POLAV | Polygonum aviculare | prostrate knotweed |
| SOLNI | Solanum nigrum | black nightshade |
| STEME | Stellaria media | chickweed |
| TRZAS | Triticum aestivum | wheat |
| ZEAMX | Zea mays | Indian corn |

The compound of Example 118, applied postemergence at a rate of 0.125 kg/ha and preemergence at a rate of 0.06 kg/ha, selectively combated unwanted plants in wheat, which suffered no appreciable damage.

Compound no. 41 proved to be suitable for combating grassy and broadleaved plants when applied postemergence at a rage of 0.125 kg/ha and preemergence at a rate of 0.04 kg/ha. Indian corn was not damaged.

Active ingredients nos. 1, 80, 93 and 16 exhibited a considerable herbicidal action at low application rates on selected plants.

In the greenhouse, grassy and broadleaved plants were safely combated by active ingredients nos. 80, 93 and 16 applied postemergence at rates of from 0.03 to 0.06 kg/ha.

Active ingredients nos. 67 and 54 proved suitable for combating a broad spectrum of weeds, including Cyperacaea, when applied postemergence at a rate of 0.125 kg/ha.

In view of the numerous application methods available, the compounds of the invention, and herbicidal agents containing them, may be used in a large number of crops for combating unwanted plants. The following may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Brassica napus var. napus | rapeseed |
| Brassica napus var. napobrassica | swedes |
| Brassica napus var. rapa | turnips |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cynodon dactylon | Bermudagrass |

-continued

| Botanical name | Common name |
|---|---|
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the active ingredients according to the invention may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamats, halocarboxylic acids, triazines, amides, ureas, diphenyl ethers, traizinones, uracils, benzofuran derivatives, quinolinecarboxylic acids, other cyclohexenone compounds, etc.

It may also be useful to apply the sulfonylureas of the formula I, ether alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Table 1

Herbicidal action on broadleaved unwanted planes and tolerance by a crop plant on postemergence application in the greenhouse of 0.125 kg/ha of compound no. 118 according to the invention

| Test plants and damage (%) | |
|---|---|
| TRZAS | 10 |
| AMARE | 95 |
| CHEAL | 98 |
| LAMAM | 100 |
| STEME | 100 |

Table 2

Control of unwanted plants and tolerance by wheat; preemergence application of 0.06 kg/ha of compound 118 according to the invention

| Test plants and damage (%) | |
|---|---|
| TRZAS | 10 |
| ECHCG | 90 |
| STEME | 100 |

Table 3

Postemergence control of unwanted plant growth in Indian corn; comparison between a compound according to the invention (A, Example 41)

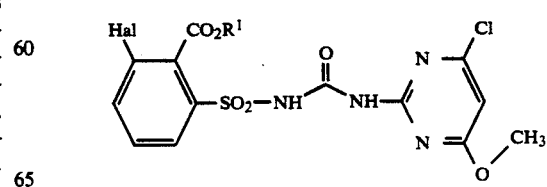

and the active ingredient Chlorimuron-ethyl (B) disclosed in U.S. Pat. No. 4,547,215

| | R¹ | Hal | kg a.i./ha | ZEAMX | ECHCG | LOLMU | AMARE | CHYCO |
|---|---|---|---|---|---|---|---|---|
| A | CH₃ | F | 0.125 | 10 | 98 | 98 | 100 | 100 |
| B | C₂H₅ | H | 0.03 | 50 | 95 | 50 | 100 | 100 |

Compound 41, when applied postemergence at a rae of 0.125 kg/ha, is suitable for combating grassy and broadleaved unwanted plants without causing any appreciable damage to Indian corn. The comparative agent Chlorimuron-ethyl did combat broadleaved plants, but at as low a rate as 0.3 kg/ha the corn is damaged to a great extent without unwanted grassy plants being combated sufficiently. This comparative experiments shows that compound 41 has significant advantages.

Table 4

Herbicidal action on grassy and broadleaved plants and tolerance by Indian corn at application rates of 0.04 kg/ha of compound 41 according to the invention

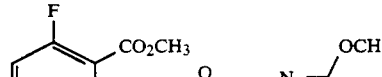

| Test plants and damage (%) | |
|---|---|
| ZEAMX | 0 |
| ECHCG | 90 |
| CHYCO | 98 |
| SOLNI | 95 |

Table 5

Herbicidal action of compounds according to the invention; preemergence application in the greenhouse

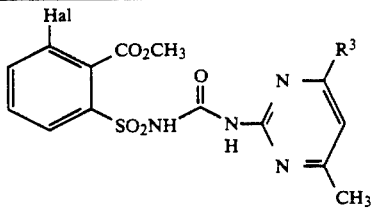

| Ex. no. | Hal | R³ | kg a.i./ha | Test plants and damage (%) | | |
|---|---|---|---|---|---|---|
| | | | | ECHCG | LOLMU | CHYCO |
| 1 | Cl | CH₃ | 0.03 | 95 | 98 | 98 |
| 80 | Cl | OCH₃ | 0.03 | 95 | 100 | 100 |
| 93 | F | OCH₃ | 0.06 | 95 | 90 | 100 |
| 16 | F | CH₃ | 0.06 | 90 | 98 | 98 |

Table 6

Herbicidal action of compounds according to the invention; postemergence application in the greenhouse

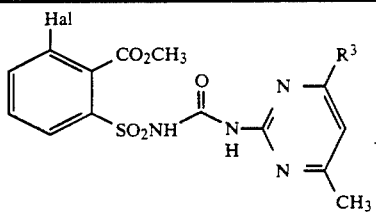

| Ex. no. | Hal | R³ | kg a.i./ha | Test plants and damage (%) | | | | |
|---|---|---|---|---|---|---|---|---|
| | | | | ECHCG | LOLMU | CHYCO | LAMAM | STEME |
| 80 | Cl | OCH₃ | 0.03 | 100 | 98 | 98 | 98 | 100 |
| 93 | F | OCH₃ | 0.06 | 98 | 95 | 100 | 100 | 100 |
| 16 | F | CH₃ | 0.06 | 98 | 95 | 100 | 100 | 98 |

Table 7

Control of unwanted broadleaved plants on postemergence application to the greenhouse of 0.125 kg/ha of compounds according to the invention

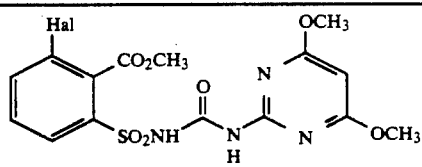

| Ex. no. | Hal | Test plants and damage (%) | | | | | |
|---|---|---|---|---|---|---|---|
| | | AMARE | CHYCO | IPOSS | LAMAM | POLAV | CYPIR |
| | F | 100 | 100 | 95 | 95 | 95 | 100 |
| | Cl | 98 | 98 | 98 | 95 | 90 | 100 |

We claim:
1. A substituted sulfonylurea of the formula I

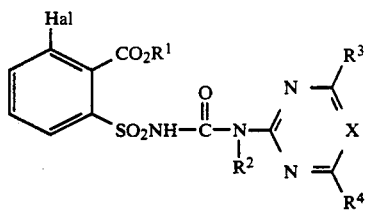

where $R^1$ is $C_1$–$C_4$-alkyl, $R^2$ is H, $R^3$ is chlorine, $R^4$ is methoxy, X is CH, Hal is fluorine or chlorine, and alkali metal and alkaline earth metal salts thereof.

2. The sulfonylurea of the formula I as defined in claim 1, wherein $R^1$ is ethyl and Hal is chlorine.

3. The sulfonylurea of the formula I as defined in claim 1, wherein $R^1$ is methyl and Hal is fluorine.

4. A composition comprising a herbicidally-effective amount of a substituted sulfonylurea described in claim 1 and an agriculturally suitable carrier therefor.

5. A composition comprising a herbicidally-effective amount of a substituted sulfonylurea described in claim 2 and an agriculturally suitable carrier therefor.

6. A composition comprising a herbicidally-effective amount of a substituted sulfonylurea described in claim 3 and an agriculturally suitable carrier therefor.

7. A method of combating the growth of unwanted plants which are located in cereal crops, which method comprises applying a herbicidally effective amount of a compound described in claim 1 to the unwanted plants.

8. A method of combating the growth of unwanted plants which are located in cereal crops, which method comprises applying a herbicidally effective amount of a compound described in claim 2 to the unwanted plants.

9. A method of combating the growth of unwanted plants which are located in cereal crops, which method comprises applying a herbicidally effective amount of a compound described in claim 3 to the unwanted plants.

* * * * *